United States Patent
George

(10) Patent No.: US 9,929,484 B1
(45) Date of Patent: Mar. 27, 2018

(54) ELECTRICAL CONNECTOR DESIGN FOR ISOLATING ELECTRICAL CONTACTS IN MEDICAL DEVICES

(71) Applicant: General Electric Company, Schenectady, NY (US)

(72) Inventor: Boban George, Bangalore (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/384,811

(22) Filed: Dec. 20, 2016

(51) Int. Cl.
*H01R 12/71* (2011.01)
*A61B 6/00* (2006.01)

(52) U.S. Cl.
CPC ......... *H01R 12/714* (2013.01); *A61B 6/502* (2013.01)

(58) Field of Classification Search
CPC .... H01R 23/722; H01R 23/725; H01R 9/096; H05K 3/368; H05K 3/308
USPC ........................................ 439/65–69, 74, 75
See application file for complete search history.

(56) References Cited

U.S. PATENT DOCUMENTS

| | | | | |
|---|---|---|---|---|
| 6,332,786 B1* | 12/2001 | Suga | ...................... | H01L 24/29 257/E21.514 |
| 6,592,783 B2* | 7/2003 | Kumakura | .................. | C09J 7/00 156/250 |
| 6,633,490 B2* | 10/2003 | Centola | .................. | H05K 3/366 174/259 |
| 6,924,654 B2* | 8/2005 | Karavakis | ............ | G01R 1/0483 324/756.03 |
| 7,052,285 B2* | 5/2006 | Wu | ......... | H05K 3/361 439/67 |
| 8,247,699 B2* | 8/2012 | Shen, Jr. | ................ | H05K 1/028 174/254 |
| 9,040,839 B2* | 5/2015 | Furuta | .................... | H05K 3/361 174/117 FF |
| 2005/0133362 A1* | 6/2005 | Van Schuylenbergh | ................... | B81C 3/002 204/192.15 |
| 2008/0182432 A1* | 7/2008 | Huang | ................ | H01L 21/4846 439/66 |
| 2010/0304580 A1* | 12/2010 | Baycura | ............... | H05K 1/0286 439/65 |
| 2013/0213693 A1* | 8/2013 | Ho | ...................... | H01L 21/4857 174/251 |
| 2014/0092576 A1* | 4/2014 | Lucero | .................. | H01L 25/167 361/783 |

(Continued)

FOREIGN PATENT DOCUMENTS

CN         102045948         5/2011

*Primary Examiner* — Gary Paumen
(74) *Attorney, Agent, or Firm* — Boyle Fredrickson, S.C.

(57) ABSTRACT

In the present invention, an electrical connector is formed with contacts on one side of a printed circuit board that are electrically coupled through the board in a known manner. A backing plate formed of a dielectric material is applied to the board over the contacts. The backing plate includes openings extending through the backing plate that are in alignment with the contacts in order to allow electrical connections to be made with the contacts, but while also isolating the contacts from the exterior surface of the backing layer. The backing layer is affixed to the board over the contacts by an adhesive resin layer having an aperture cut into the layer. The aperture cut into the layer surrounds the contacts on the board, and due to the low or no flow nature of the resin, does not flow onto the contacts to cover the contacts.

13 Claims, 7 Drawing Sheets

(56) References Cited

U.S. PATENT DOCUMENTS

2014/0346451 A1* 11/2014 Oh ..................... H01L 51/5246
　　　　　　　　　　　　　　　　　　　　　257/40

* cited by examiner

ELECTRICAL CONNECTOR DESIGN FOR ISOLATING ELECTRICAL CONTACTS IN MEDICAL DEVICES

BACKGROUND OF INVENTION

The invention relates generally to electrical connectors and more particularly to electrical connectors including circuit boards used as electric contacts in medical imaging devices.

Medical imaging devices are utilized in a wide range of situations in order to obtain images of the tissue of interest within a patient in order to determine the proper treatment for the condition of the individual as determined by the images.

These imaging devices require power in order for their operation. Power is normally supplied in the form of electric current obtained from a suitable power outlet located in the vicinity of the imaging device being utilized. The current is directed into the imaging device by a suitable electrical connection, such as a conventional plug and socket connection, made between the power source and the imaging device.

In many imaging devices, electrical connections are additionally made between the imaging device and various attachments that are connected to the imaging device. In these imaging devices, the power supplied to the imaging device from the power outlet can be routed through the imaging device not only to power the imaging device, but to supply power to the various attachments to the imaging device.

As these imaging devices and the attachments to the imaging devices can and do come into contact with the patient, there are many requirements with regard to the safety of the patient for the isolation of the current supplied to the imaging device from the patient. Thus, with the electrical connections made between the attachments and the imaging device, these connections often utilize constructions that provide effective electrical isolation of the contacts for the electrical connections to be made, thereby preventing inadvertent contact with the contacts.

In one example of a prior art electrical connection, as shown in FIG. 1, a printed circuit board (PCB) 1000 is constructed to provide vias 1002 within the board 1000 that isolate the contacts 1004 from the exterior of the board 1000, and thus from contact with the patient. In step 1 of forming the board 1000, initially the electric surface mount contacts 1004 are printed or otherwise applied to SMD pads 1006 positioned on a board 1008. In step 2, a second board 1010 is positioned over and in alignment with the first board 1008, where the second board 1010 forms the isolation layer separating the contacts 1004 from the exterior of the PCB 1000. In step 3, mechanical drilling is used to form vias 1002 through the board 1010, but that stop short of the contacts 1004 to avoid damage to the contacts 1004. In step 4, laser drilling is utilized to expose the contacts 1004 within the board 1010, thereby allowing electrical connections to be made by the insertion of suitable conductive structures (not shown) into the vias 1002 which are held in electrical connection with the contacts by frictional engagement with the vias 1002.

However, in this manufacturing method for the PCBs 1000, the laser drilling in step 4 often resulted in overdrilling at the bottom of the vias 1002, due to the fact that the lasers used in the drilling are not completely oriented perpendicularly to the board 1010. As such, the lasers would drill laterally into the board 1010 and expose the sides of the contacts 1004, which significantly degrades the electric connections to be made with the vias 1002.

In an attempt to remedy this issue, a prior art solution was to form the pads 1006 larger than the contacts 1004. In this construction the pads 1006 would prevent the lasers from drilling around the sides of the contacts 1004 due to the presence of the larger pads 1006 around the contacts 1004.

However, while the prior art solution of the use of larger pads 1006 prevented the overdrilling of the vias 1002 within the PCB 1000, the prior art PCBs 1000 still required a complex, four step construction process in order to create the desired construction for the isolation of the contacts 1004 on the PCBs 1000.

Accordingly, it is desirable to develop a system and method for the construction of a PCB that electrically isolates the contacts on the PCB but with a simpler construction and manufacturing process.

BRIEF DESCRIPTION OF THE INVENTION

There is a need or desire for a simplified PCB capable of electrically isolating the electric contacts on the PCB from contact by an operator. The PCB and method for forming the PCB includes forming contacts on one side of a board that are electrically coupled through the board in a known manner. A backing plate formed of a dielectric material is then applied to the board over the contacts. The backing plate includes openings extending through the backing plate that are in alignment with the contacts in order to allow electrical connections to be made with the contacts, but while also isolating the contacts from the exterior surface of the backing layer. The backing layer is affixed to the board over the contacts by a resin layer having an aperture cut into the layer. The resin layer is a low or no flow polymer material that can be used to adhere the backing layer to the board. The aperture cut into the layer surrounds the contacts on the board, and due to the low or no flow nature of the resin, does not flow onto the contacts to cover the contacts when pressure and/or heat is applied to the backing layer and resin layer to form the adhesive bond between the board and the backing layer using the resin layer. This two layer PCB construction significantly simplifies the overall construction and manufacturing process for the formation of a PCB that provides effective isolation of the contacts on the board from any operator contacting the board while still enabling effective electrical connections to be made with appropriately configured connectors.

According to one exemplary and non-limiting embodiment of the invention, a method for forming an electrical connector for a medical device with isolated electrical contacts includes the steps of forming a first board including a number of electrical contacts thereon, forming a second board with a number of openings therein disposed in alignment with the contacts on the first board and securing the second board to the first board using an adhesive layer positioned between the first board and the second board.

According to another exemplary and non-limiting embodiment of the invention, an electrical connector for a medical device includes a first board including a number of electrical contacts thereon, an adhesive layer disposed on the first layer around the electrical contacts; and a second board positioned on the adhesive layer opposite the first board, the second board including a number of openings disposed in alignment with the contacts.

According to another exemplary and non-limiting embodiment of the invention, a medical device attachable to a medical imaging system including a pin connector, the device comprising an electrical connector that is releasably engageable with the pin connector, the electrical connector including a first board including a number of electrical contacts thereon, an adhesive layer disposed on the first layer around the electrical contacts; and a second board positioned on the adhesive layer opposite the first board, the second board including a number of openings disposed in alignment with the contacts, wherein the adhesive layer and the second board position the contacts in a recessed location within the electrical connector.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 1:
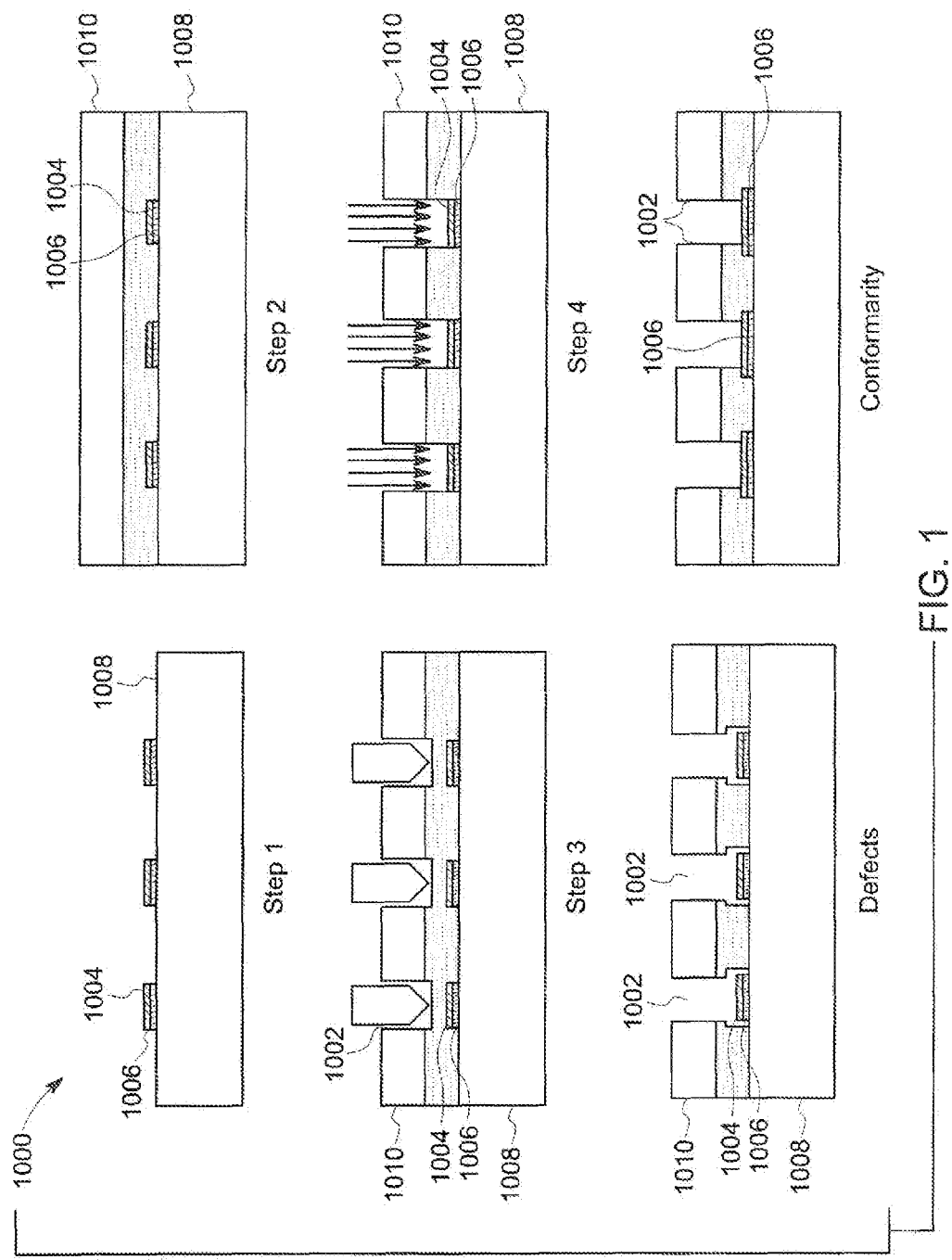
FIG. 1 is a schematic representation of prior art PCB constructions and manufacturing methods.
Figure 2:
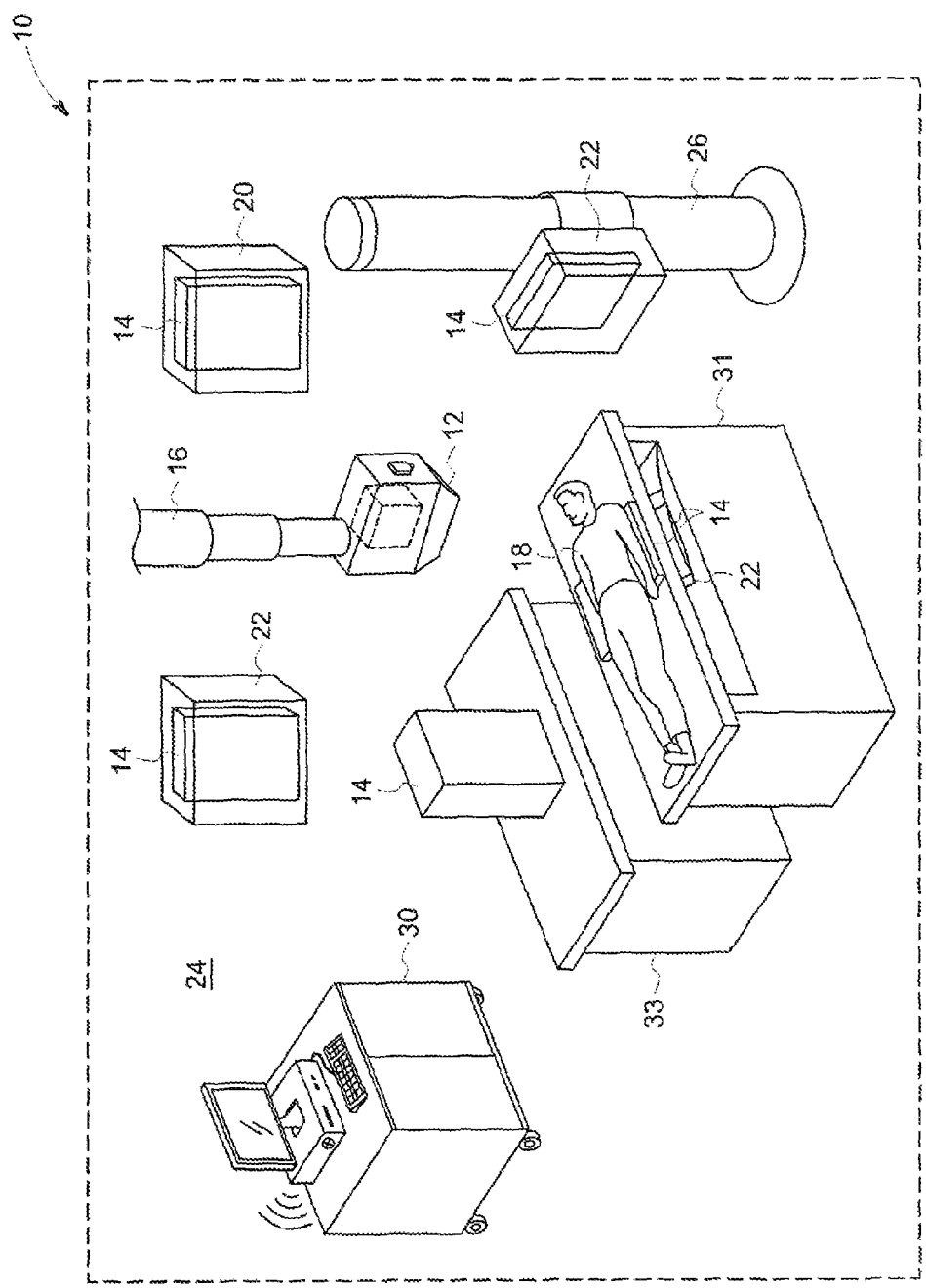
FIG. 2 is a pictorial view of a medical imaging system formed according to an exemplary non-limiting embodiment of the invention.

Referring to the drawings, FIG. 1 is a pictorial view of an exemplary imaging system 10 formed in accordance with an embodiment of the present invention. FIG. 2 is a block schematic diagram of the exemplary imaging system 10 shown in FIG. 1. Various embodiments of the invention may be used with the exemplary medical imaging system 10 as shown in FIG. 1. The medical imaging system 10 may be any type imaging system such as, for example, an x-ray imaging system or a tomosynthesis imaging system. Moreover, the various embodiments are not limited to medical imaging systems for imaging human subjects, but may include veterinary or non-medical systems for imaging non-human objects, or non-destructive testing systems (e.g. airport baggage systems) etc.

The medical imaging system 10 in the preferred embodiment is a digital radiography imaging system 10 that includes an x-ray source 12 and at least one detector 14. In the exemplary embodiment, the detector 14 is a portable x-ray detector. As shown in FIG. 2, the detector 14 may be utilized in various locations and applications, and in either a fixed state or a portable state. The x-ray source 12 is mounted to a gantry 16. The gantry 16 may be movable to enable the x-ray source 12 to be properly positioned with respect to a subject 18 being imaged or to enable the x-ray source 12 to be moved from one imaging room to another. Optionally, the gantry 16 may be stationarily mounted by coupling the gantry to a floor or ceiling, for example.

The detector 14 may be operated in a fixed state or a portable state. In one mode of operation, when the detector 14 is operated in the fixed state, the detector 14 is installed in a cassette holder 22. The cassette holder 22 may also be referred to herein as a bucky. The cassette holder 22 is mounted or attached to a fixed location. For example, as shown in FIG. 2, the cassette holder 22 may be coupled to a wall 24 or a post 26. One exemplary and non-limiting embodiment of an imaging system 10 utilizing this configuration is a digital mammography system 300, shown in FIG. 3. The system 300 includes a post or pedestal 302 on which is positioned a moveable gantry 304. The gantry 304 supports an x-ray source 305 at one end and a compression device 306 at the opposite end. The gantry 304 can move vertically and rotate with regard to the pedestal 302 in order to locate the compression device 306 at the proper location. The compression device 306 includes a compression paddle 308 that is vertically movable with regard to the gantry 304 and a bucky 310 and associated detector 14 disposed on the gantry 304 below the paddle 308. The movement of the compression paddle 308 and gantry 304 as well as the operation of the x-ray source 305 is controlled by one or more footswitches 312 operably connected to the pedestal 302.

When the cassette holder 22 is coupled to the wall 24 or the post 26, the cassette holder 22 is often referred to as a wall bucky. Moreover, the cassette holder 22 may fixedly installed in an imaging table 31. When installed in the imaging table 31, the cassette holder 22 may be referred to as a table bucky. In the fixed state, the detector 14 receives power from the cassette holder 22.

The cassette holder or bucky 22 also enables the x-ray detector to communicate with an imaging workstation, such as an imaging workstation 30. During operation, infomnation is transmitted from the workstation 30 to the detector 14 via wires (such as an Ethernet cable) in the cassette holder 22. Additionally, information generated by the detector 14 may be transmitted to the workstation 30 via wires (such as an Ethernet cable) in the cassette holder 22. The information that is generated and transferred may be at a rate higher than a wireless connection can support. Accordingly, in the fixed state, the detector 14 is mounted in a fixed position to the cassette holder 22 and power and communication signals are transmitted from, and received by the detector 14 via the cassette holder 22.

In another mode of operation, the detector 14 is operated in the portable state. For example, in the portable state, the detector 14 is installed into a charging bin 20. The charging bin 20 is configured to provide power to the detector 14 to charge a battery (not shown) installed in the detector 14, but does not provide a wired communication path between the detector 14 and the imaging workstation 30. In another portable state, the detector 14 receives operational power from the battery installed in the detector 14. This portable state is also referred to herein as digital cassette mode. Additionally, operational and communication signals are transmitted wirelessly between the detector 14 and the workstation 30. For example, as shown in FIG. 1, in the portable state, the detector 14 may be positioned on a table 31 beneath the subject 18. The detector 14 may also be positioned on a separate table 33 that is adjacent to the subject 18. Accordingly, in the portable state, the detector 14 is not coupled to the cassette holder 22.

Figure 4:
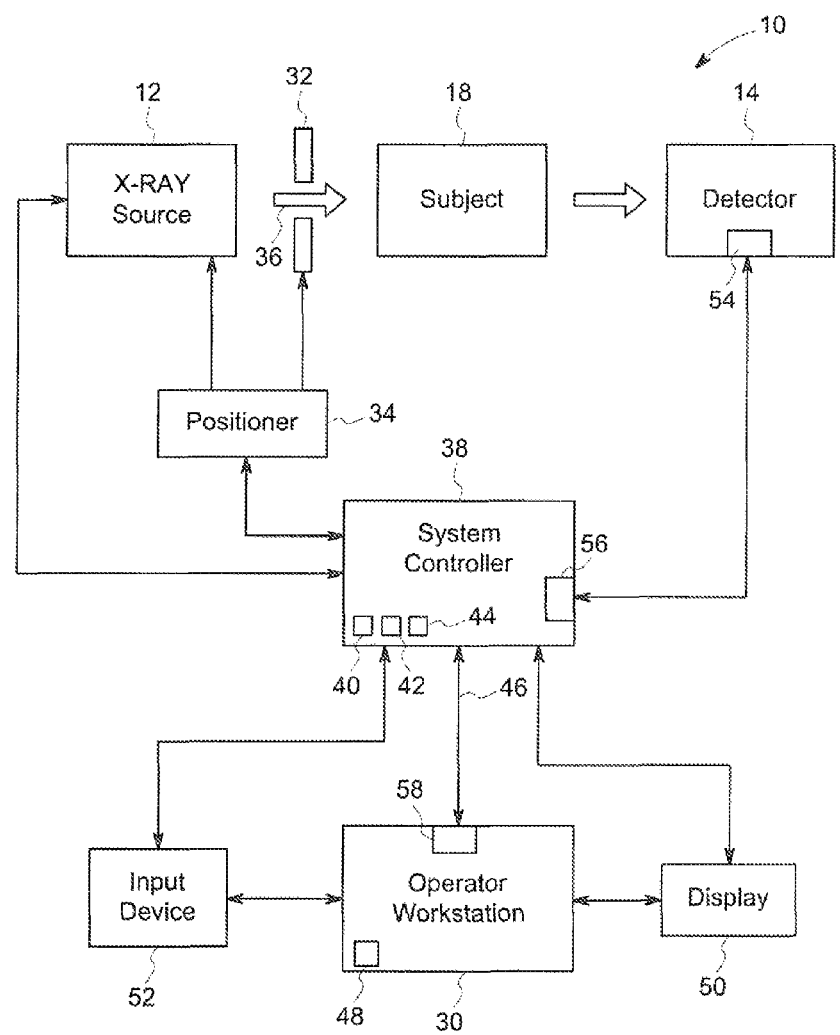
FIG. 4 is a block schematic diagram of the medical imaging system shown in FIG. 2 according to an exemplary non-limiting embodiment of the invention.

Referring to FIG. 4, the imaging system 10 may also include a collimator 32 that is disposed between the x-ray source 12 and the subject 18. The imaging system 10 may also include a positioner 34. The positioner 34 is a mechanical controller coupled to the x-ray source 12 and the collimator 32 for controlling the positioning of the x-ray source 12 and the collimator 32. During operation, the imaging system 10 generates images of the subject 18 by means of an x-ray beam 36 emitted by the x-ray source 12, and passing through the collimator 32. The collimator 32 forms and confines the x-ray beam 36 to a desired region, wherein the subject 18, such as a human patient, an animal or an object, is positioned. A portion of the x-ray beam 36 passes through or around the subject 18 and, being altered by attenuation and/or absorption by tissues within the subject 18, continues on toward and impacts the detector 14. The detector 14 converts x-ray photons received on its surface to lower energy light photons, and subsequently to electric signals, which are acquired and processed to reconstruct an image of internal anatomy of the subject 18.

The imaging system 10 further includes a system controller 38 coupled to the x-ray source 12, the detector 14, and the positioner 34 for controlling operation of the x-ray source 12, the detector 14, and the positioner 34. It should be realized that the system controller 38 is configured to transmit and receive information from the detector 14, the detector 14 is manually positioned by the operator, when the detector is operated as a digital cassette, or when the operator places the detector in a cassette holder. The system controller 38 may supply both power and control signals for imaging examination sequences when the detector is operated in the fixed state. In general, the system controller 38 controls the operation of the imaging system 10 to execute examination protocols and to process acquired image data. The system controller 38 may also include signal processing circuitry, based on a general purpose or application-specific computer, associated memory circuitry for storing programs and routines executed by the computer, as well as configuration parameters and image data, interface circuits, and so forth.

The system controller 38 may further include at least one computer or processor 40 that is configured to coordinate the operation of the x-ray source 12, the detector 14, and the positioner 34, and to process image data acquired from the detector 14. As used herein, the term "computer" or "processor" may include any processor or processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer". During operation, the processor 40 carries out various functions in accordance with routines stored in an associated memory circuitry 42. The associated memory circuitry 42 may also store configuration parameters, imaging protocols, operational logs, raw and/or processed image data, and so forth.

The system controller 38 may further include interface circuitry 44 that permits an operator or user to define imaging protocols, imaging sequences, determine the operational status and health of system components, and so-forth. The interface circuitry 44 may allow external devices to receive images and image data, and command operation of the radiography system, configure parameters of the system, and so forth. The system controller 38 may be coupled to a range of external devices via a communications interface. Such devices may include, for example, the operator workstation 30 for interacting with the system controller 38 or directly with the detector 14, processing or reprocessing images, viewing images, and so forth.

The operator workstation 30 may be embodied as a personal computer (PC) that is positioned near the imaging system 10 and hard-wired to the system controller 38 via a communication link 46. The workstation 30 may also be embodied as a portable computer such as a laptop computer or a hand-held computer that transmits information to the system controller 38. In one embodiment, the communication link 46 may be hardwired between the system controller 38 and the workstation 30. Optionally, the communication link 46 may be a wireless communication link that enables information to be transmitted to or from the workstation 30 to the system controller 38 wirelessly. In the exemplary embodiment, the workstation 30 controls real-time operation of the imaging system 10. The workstation 30 is also programmed to perform medical image diagnostic acquisition and reconstruction processes described herein.

The operator workstation 30 includes a central processing unit (CPU) or computer 48, a display 50 and an input device 52. In operation, the computer 48 executes a set of instructions that are stored in one or more storage elements or memories, in order to process input data. The storage elements may also store data or other information as desired or needed. The storage elements may be in the form of an information source or a physical memory element within the computer 48. The set of instructions may include various commands that instruct the processor 48 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The CPU 48 receives inputs, e.g., user commands, from the input device 52. The input device 52 may be, for example, a keyboard, a mouse, a touch-screen panel, and/or a voice recognition system, etc. Through input device 52 and associated control panel switches, the operator can control the operation of the imaging system 10 and the positioning of the x-ray source 12 for a scan. Similarly, the operator can control the display of the resulting image on the display 50 and can perform image-enhancement functions using programs executed by the workstation CPU 48. The workstation 30 may also be linked to the system controller 38 by one or more network links.

In the exemplary embodiment, to transmit the information from the detector 14 to the system controller 38 or the workstation 30, when the detector 14 is operating in the portable state, the detector 14 includes a transceiver 54. The transceiver 54 enables the detector information to be transmitted wirelessly to a corresponding transceiver 56 that is mounted in the system controller 38. Optionally, the transceiver 54 is configured to transmit the detector information in a wireless format to a corresponding transceiver 58 that is mounted in the workstation 30.

Figure 3:
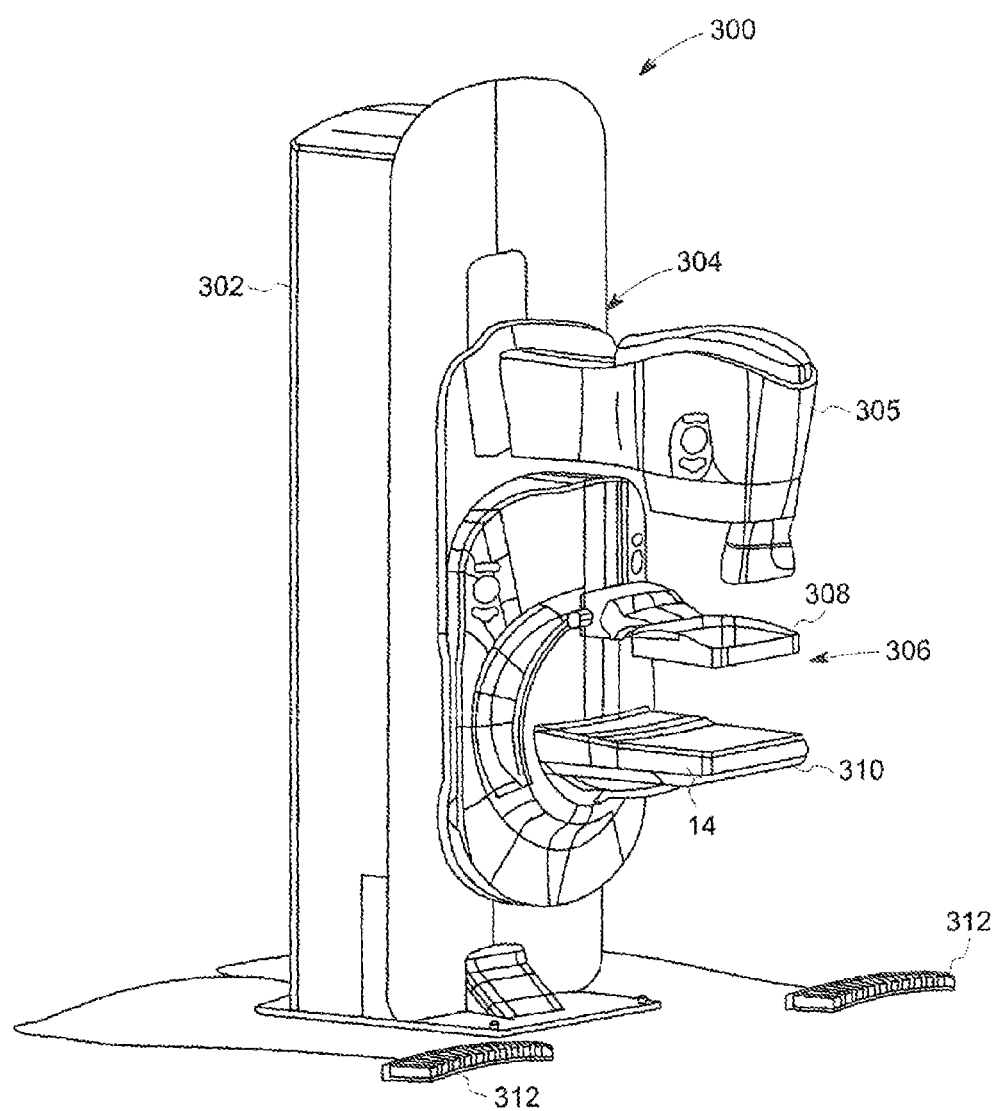
FIG. 3 is an isometric view of a medical imaging system according to an exemplary non-limiting embodiment of the invention.
Figure 5:
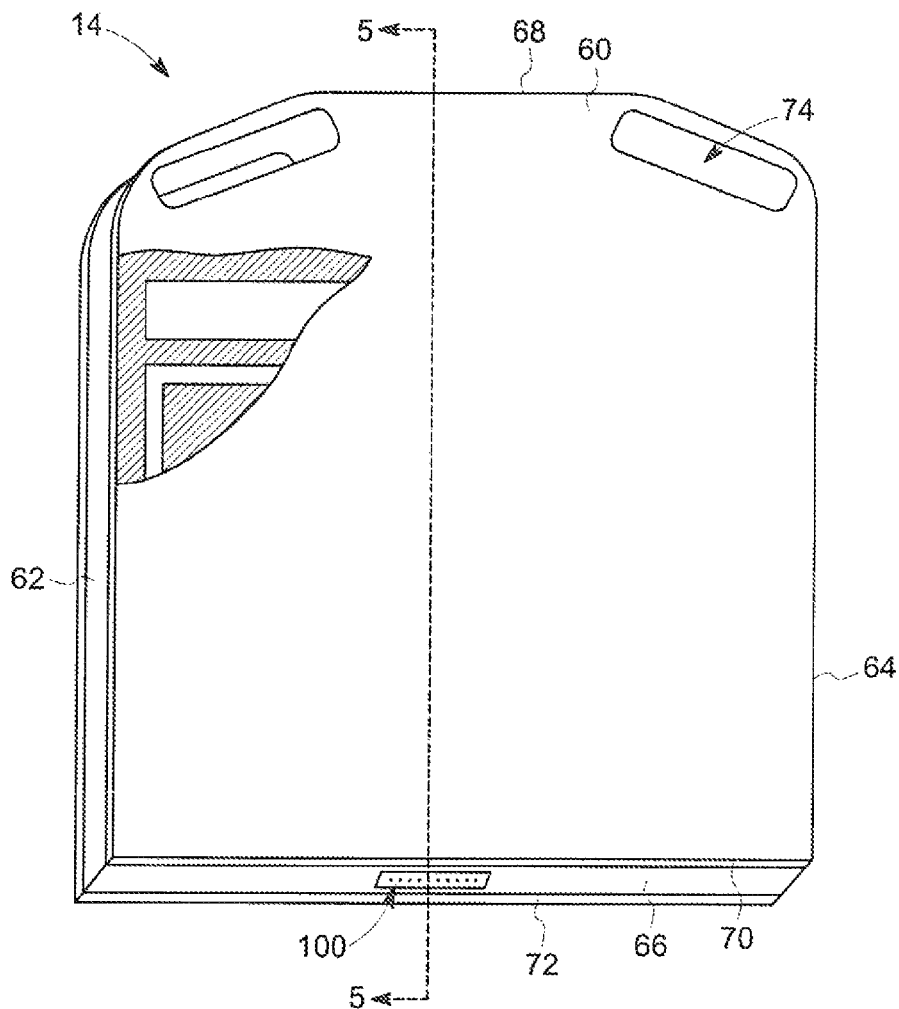
FIG. 5 is a top cut-away view of a portable x-ray detector according to an exemplary non-limiting embodiment of the invention.

FIG. 5 is a top cut-away view of the portable detector 14 shown in FIGS. 2-3. The detector 14 includes a casing 60. The casing 60 is formed to include a pair of sidewalls 62 and 64, a bottom side 66, and an opposing top side 68. The casing 60 also includes a front cover 70, shown as a surface parallel to the plane of the illustration, and an opposing back cover 72. The casing 60 also includes a handle 74 that extends from the front cover 70 to the back cover 72. During operation, the handle 74 enables an operator to transport the portable detector 14 from one location to another. Specifically, the handle 74 can be used to facilitate mounting, carrying and/or storing the portable detector 14. The sidewalls, top and bottom walls, the front and back covers together form the casing 60. The casing 60 may be made of a lightweight, low atomic number (N) material, such as aluminum, or a graphite material. Graphite has a lower weight than aluminum, but it is also stiffer and less energy-absorbent.

Figure 6:
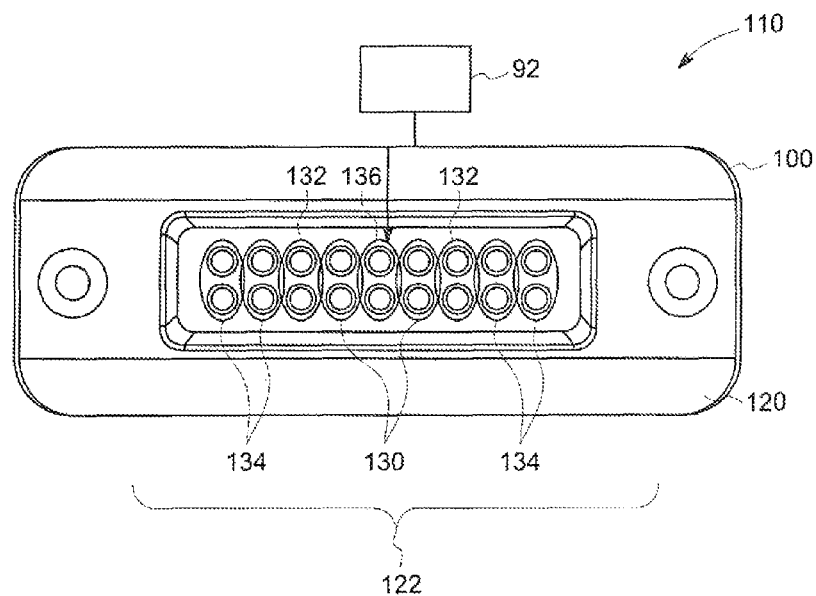
FIG. 6 is a pictorial illustration of an exemplary detector docking connector according to an exemplary non-limiting embodiment of the invention.

The portable detector 14 also includes a docking connector 100 shown in FIG. 6. The docking connector 100 is configured to mate with various other connectors. For example, the docking connector 100 is configured to mate with a charging connector 140 that is installed on the charging bin 20 and a bucky connector 160 (shown in FIG. 7) that is installed on the cassette holder 22. The charging connector 140 and the bucky connector 160 are similarly constructed and are described in more detail below.

FIG. 6 is a front view of the exemplary docking connector 100. The docking connector 100 includes a connector housing 120 and a plurality of docking connector contacts or pins 122 that are installed in the connector housing 120. As discussed above, the docking connector 100 is configured to mate with the charging connector 140 that is installed on the charging bin 20 and also mate with the bucky connector 160 that is installed on the cassette holder 22. In one embodiment, the docking connector pins 122 are fabricated from a conductive tubular material to enable the docking connector pins 122 to be inserted into complementary openings of either the charging connector 140 or the bucky connector 160 to engage electrical contacts formed and/or disposed within the either the charging connector 140 or the bucky connector 160.

In the exemplary embodiment, the docking connector 100 includes a plurality of power supply pins 130. The power supply pins 130 are configured to receive power from the charging bin 20 when the detector 14 is installed in the charging bin 20. The power supply pins 130 are also configured to receive power from the cassette holder 22 when the detector 14 is installed in the cassette holder 22. In one embodiment, the docking connector 100 includes at least one power supply pin 130. In the exemplary embodiment, the docking connector 100 includes four power supply pins 130. During operation, the charging bin 20 and the cassette holder 22 are each configured provide approximately 48 volts DC to the detector 14 via four (4) power supply pins 130, (two (2) pins 130 to supply power and two (2) pins for functioning as ground). In the exemplary embodiment, utilizing four power supply pins 130 reduces the amount of voltage drop across the mated connector. Each mated pin pair represents resistance between the source (the power supply) and the load (the detector). Using more than one pin pair decreases the total resistance.

During operation, the voltage drop across a resistor is proportional to the current (drawn by the load, the detector), therefore increasing the number of pin pairs in the mated connector decreases the resistance and therefore the voltage drop across the mated connector between the power supply and the detector. As such, each mated pin pair conducts a portion of the current drawn by the detector, example, utilizing two pin pairs enables each mated pin pair to supply nominally one half of the power to the detector. Furthermore, increasing the quantity of power supply pins 130 utilized to conduct power to the portable detector 14 substantially reduces the possibility of an electrical arc occurring at the docking connector 100, when the portable detector 14 is coupled or uncoupled from either the charging bin 20 or the cassette holder 22. It should be realized that although the exemplary embodiment illustrates the docking connector 100 as including four power supply pins 130, the docking connector 100 may include fewer than four or greater than four power supply pins 130. Accordingly, in the exemplary embodiment, the docking connector 100 includes N=2 power supply pins 130.

As shown in FIG. 6, the docking connector 100 also includes a plurality of power return pins 132. The power return pins 132 are configured to provide an electrical power return pathway from the portable detector 14 back to either the charging bin 20 when the detector 14 is installed in the charging bin 20 or the cassette holder 22 when the detector 14 is installed in the cassette holder 22. In the exemplary embodiment, the docking connector 100 also includes N power return pins 132, where in the exemplary embodiment, N=2.

The docking connector 100 also includes a plurality of Ethernet pins 134 for forming one or more Ethernet ports. The Ethernet pins 134 are configured to receive and transmit information from the detector 14 to the imaging system 10 via the cassette holder 22. The docking connector 100 further includes a pair of detector state pins 136. The detector state pins 136 are utilized by the processor 92 to enable the processor 92 to determine whether the detector 14 is installed in the charging bin 20 or the cassette holder 22.

Figure 7:
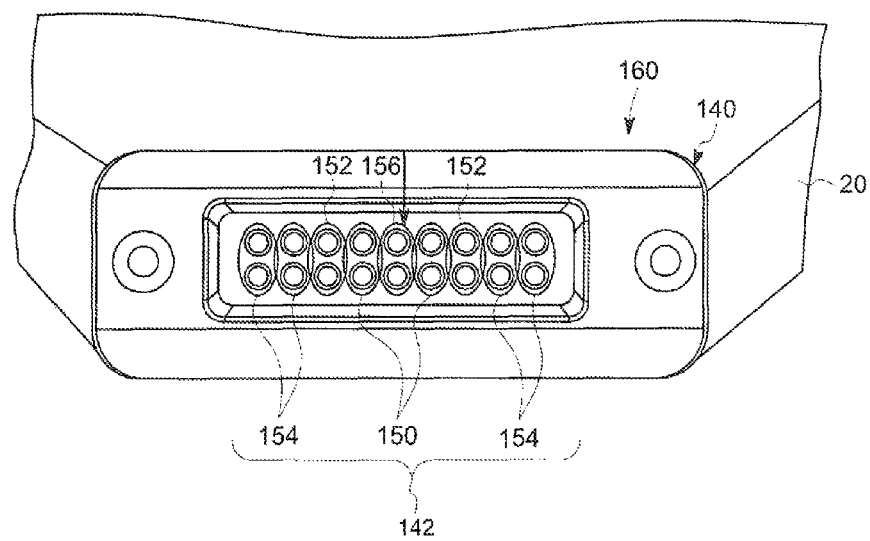
FIG. 7 is a front view of an exemplary charging connector and/or bucky connector that may be used with the detector docking connector shown in FIG. 5 in accordance with various embodiments.

FIG. 7 is front view of an exemplary charging connector 140 formed to be complementary to the docking connector 100 and that may be installed in the charging bin 20. In the exemplary embodiment, when the portable detector 14 is installed in the charging bin 20, or coupled to the charging bin 20, the charging connector 140 is configured to mate with the docking connector 100 to enable power to be transmitted between the portable detector 14 and the charging bin 20. FIG. 7 also illustrates the construction of a bucky connector 160 that may be installed in the cassette holder 22. In the exemplary embodiment, when the portable detector 14 is installed in the cassette holder 22, or coupled to the cassette holder 22, the bucky connector 160 is configured to mate with the docking connector 100 to enable power and information to be transmitted between the portable detector 14 and the cassette holder 22. Accordingly the charging connector 140/bucky connector 160 is substantially similar to the docking connector 100 in size and shape to enable the charging connector 140/bucky connector 160 to mate with the docking connector 100. The charging connector 140/bucky connector 160 includes a plurality of contacts 142. The contacts 142 are configured to be contacted and engaged by the docking connector pins 122 installed on the docking connector 100, or vice versa.

The charging connector 140/bucky connector 160 also includes a plurality of power supply contacts 150. The power supply contacts 150 are configured to conduct power from charging bin 20 when the detector 14 is installed in the charging bin 20 to the docking connector 100 and thus to the portable detector 14. In the exemplary embodiment, the charging connector 140/bucky connector 160 includes N power supply contacts 150, wherein N=2. As discussed above, during operation approximately one half of the total power supplied to the portable detector 14 is conducted through each power supply contact 150 to a respective power supply pin 130 in the docking connector 100.

The charging connector 140/bucky connector 160 also includes a plurality of power return contacts 152 that provide the return power pathway from the portable detector 14, via the power return pins 132, back to the charging bin 20 when the detector 14 is installed in the charging bin 20. The charging connector 140/bucky connector 160 may also include a plurality of Ethernet contacts 154. The Ethernet contacts 154 are configured to mate with the Ethernet pins 134 to form Ethernet ports that enable information to be transmitted and received between the detector 14 and the imaging system 10.

The charging connector 140/bucky connector 160 further includes a pair of detector state contacts 156. The detector state contacts 156 are used in conjunction with the detector state pins 136 to enable the processor 92 to determine whether the portable detector 14 is installed in the charging bin 20 or the cassette holder 22.

Figure 8:
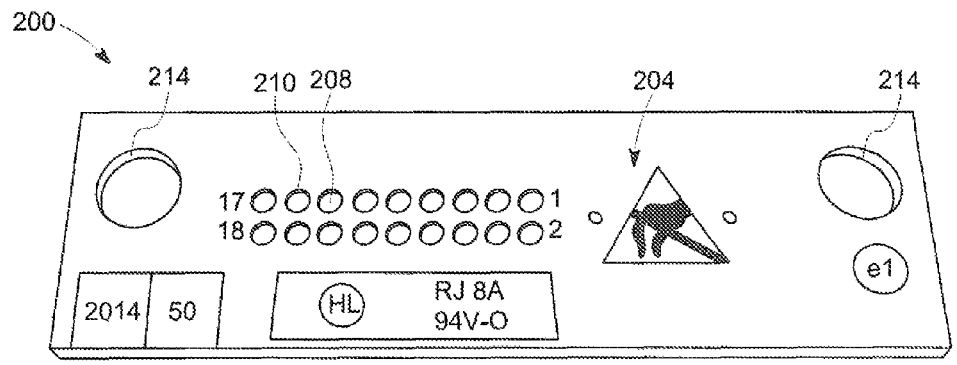
FIG. 8 is a perspective view of an electrical connector including a printed circuit board (PCB) constructed according to another exemplary non-limiting embodiment of the invention.
Figure 9:
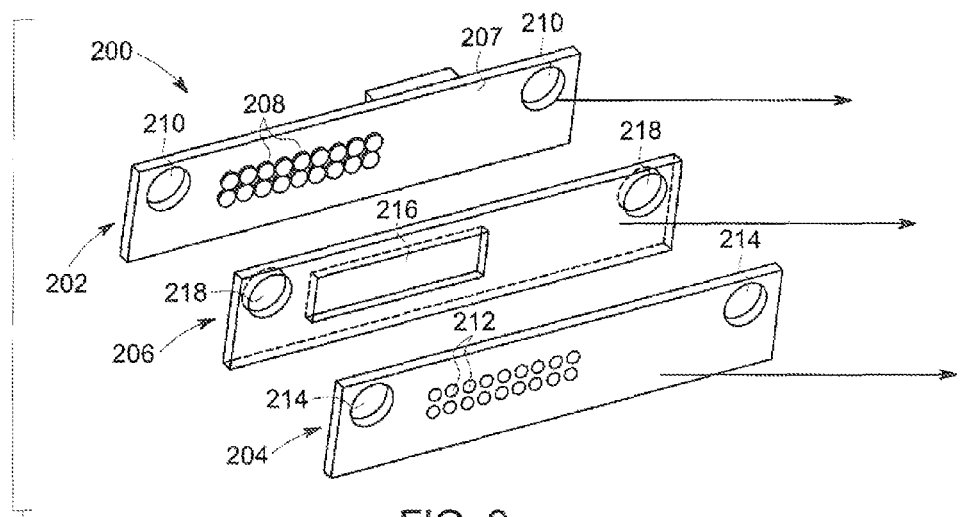
FIG. 9 is an exploded, isometric view of the electrical connector of FIG. 8.

Looking now at FIGS. 8 and 9, one exemplary non-limiting embodiment of a PCB 200 used to form the docking connector 100, the charging connector 140 and/or the bucky connector 160 is illustrated. The PCB 200 is formed of a first rigid dielectric layer or board 202, that is not formed of a metal, a second rigid dielectric layer or board 204, that is not firmed of a metal, and an adhesive layer 206 disposed therebetween.

First board 202 can be a single or multi-layer board and is formed of any suitable dielectric material other than a metal, with a thickness in the range of 1.0 mm-1.5 mm and includes a number of contacts 208 formed thereon. In addition, the board 202 includes a number of bores 210 that are used to engage suitable locking features (not shown) to hold the PCB 200 including the board 202 where desired. The board 202 and contacts 208 are formed in any suitable manner, using standardized subtractive, semi-additive or additive methods and techniques for printing or otherwise applying the materials forming the contacts 208 onto one surface 207 of the non-metal board 202. In one exemplary and non-limiting embodiment of the invention, initially the board 202 is formed in an additive manufacturing process with one or more layers of a conductive film (not shown), such as a gold film and/or a copper film, applied to a surface 207 of the board 202. (is this correct?) Subsequently, any required bores or vias (not shown) are drilled through the board 202 and filled with a conductive material (not shown) in order to provide a path for connecting the contacts 208 to components (not shown) on the opposite side of the board 202. The conductive film is then etched into the desired configuration for the contacts 208 in a conventional manner utilizing one or more resist layers (not shown) and etching materials to form the board 202 and contacts 208 on the surface 207. The board 202 is then finished, such as in one exemplary and non-limiting embodiment by plating the board 202 with an electroless nickel immersion gold coating (not shown) to form a coating of 0.04-0.06 microns of gold over 3.0-6.0 microns of nickel on the non-contact areas of the board 202, and/or a solder mask (not shown), which can be applied only to the board 202 opposite the surface 207. In the exemplary illustrated embodiment, the contacts 208 can be formed as flat contacts that are formed directly onto the first board 202, with suitable circuits (not shown) and other components (not shown) operably connected to the contacts 208 using the vias and disposed on the first board 202 opposite the contacts 208.

Once the contacts 208 are formed on the non-metal board 202, the second board or dummy PCB/backing layer or plate 204 is formed of a non-metal material having a thickness of between 0.5 mm-1.0 mm. The second board/backing plate 204 in one exemplary embodiment is formed of a dielectric material and/or an etched epoxy laminate including a number of openings 212 that are aligned with the contacts 208 when the boards 202 and 204 are placed over one another. The board 212 also includes bores 214 that are similarly formed to bores 210 in board 202 in order to provide the positioning function for placement of the PCB 200.

To secure the board 202 to the board 204 and form the PCB 200, the adhesive layer 206 is positioned between the boards 202 and 204. Adhesive layer 206 is formed with a thickness of between 0.05 mm-0.2 mm of a suitable resin, such as a low or no flow prepreg resin material, including but not limited to polyimide resins, e.g., 38N from Arlon Electronic Materials. The adhesive layer 206 that is formed with an aperture 216 having a shape with a perimeter larger than the perimeter of the area encompassing the contacts 208 and openings 212, as well as bores 218 formed similarly to bores 210,214 in boards 202,204. The adhesive layer 206 is compressed between the boards 202,204 in an additive manufacturing technique under suitable temperatures, e.g., platen temperatures between 360° F. and 380° F., and pressures, e.g., between 180 psi to 350 psi, in order to enable the layer 206 to bond to each of the boards 202,204. Further, the nature of the material forming the layer 206 prevents the material from spreading out to cover any portion of the contacts 208 or openings 212, thereby defining a space between the boards 202,204 that provides clean contact with the contacts 208 for any pin (not shown) engaged with the contact 208 through the openings 212. Further, the bores 202,204 also remain unobstructed due to the presence of the bores 218 in the layer 206. In addition, due to the presence of the board 204 secured by layer 206, direct contact with the electrical contacts 208 on the board 202 is prevented other than by pins (not shown) disposed on a suitable complementary connector (not shown) that is engaged with the PCB 200 in a known manner.

After the bonding the boards 202,204 to one another using the layer 206, a 2-layer electrical connector/PCB 200 is formed, which has a greatly simplified manufacturing process and construction compared with the prior art 4-layer high density interconnect boards 1000.

While the electrical connector/PCB 200 has been illustrated as being utilized to form isolated electrical connections in medical imaging devices, and components therefor, such as for bucky panel connectors, the electrical connector/PCB 200 can be utilized as a connector for other medical devices such as in paddles for mammography devices, among others.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for forming an electrical connector for a medical device with isolated electrical contacts; the method comprising the steps of:
   forming a first board including a number of electrical contacts thereon;
   forming a second board with a number of openings therein disposed in alignment with the contacts on the first board; and
   securing the second board to the first board using an adhesive layer positioned between the first board and the second board;
   wherein the adhesive layer is formed of a layer of prepreg material and the step of securing the second board to the first board comprises the steps of:
      forming the layer of prepreg material;
      placing the prepreg material layer between the first board and the second board; and
      compressing the first board and second board against one another, and
   wherein the step of forming the layer of prepreg material comprises forming an aperture in the layer to be positioned in alignment with the contacts on the first board and the openings in the second board.

2. A method for forming an electrical connector for a medical device with isolated electrical contacts; the method comprising the steps of:
   forming a first board including a number of electrical contacts thereon;
   forming a second board with a number of openings therein disposed in alignment with the contacts on the first board; and
   securing the second board to the first board using an adhesive layer positioned between the first board and the second board;
   wherein the adhesive layer is formed of a layer of prepreg material and the step of securing the second board to the first board comprises the steps of:
      placing the prepreg material layer between the first board and the second board; and
      compressing the first board and second board against one another, and
   wherein the step of compressing the first board and second board against one another comprises preventing the prepreg layer from flowing between the contacts on the first board and the openings in the second board.

3. The method of claim 2 wherein the step of compressing the first board and second board against one another further comprises heating the prepreg layer in conjunction with compressing the first board and the second board.

4. The method of claim 2 further comprising the step of forming the layer of prepreg material prior to placing the prepreg material between the first board and the second board.

5. The method of claim 2 wherein the step of preventing the prepreg layer from flowing between the contacts and the openings comprises forming an aperture in the prepreg layer having a perimeter larger than a perimeter defined by the combined area encompassing the contacts and the openings.

6. The method of claim 5 wherein the step of preventing the prepreg layer from flowing between the contacts and the openings further comprises forming the prepreg layer of a no flow prepreg material.

7. An electrical connector for a medical device, the electrical connector comprising:
   a first board including a number of electrical contacts thereon;
   an adhesive layer disposed on the first board around the electrical contacts; and
   a second board positioned on the adhesive layer opposite the first board, the second board including a number of openings disposed in alignment with the contacts, wherein the adhesive layer includes an aperture having a perimeter greater than an area surrounding the contacts on the first board and the openings in the second board.

8. The electrical connector of claim 7 wherein the adhesive layer comprises a no flow prepreg material.

9. The electrical connector of claim 7 wherein the no flow prepreg material is selected a polyimide.

10. The electrical connector of claim 7 wherein the thickness of the adhesive layer is between 0.5 mm and 1.0 mm.

11. The electrical connector of claim 7 wherein the first board and the second board are each formed of a non-metal material.

12. A medical device attachable to a medical imaging system including a pin connector, the device comprising an electrical connector that is releasably engageable with the pin connector, the electrical connector including a first board including a number of electrical contacts thereon, an adhesive layer disposed on the first layer around the electrical contacts; and a second board positioned on the adhesive layer opposite the first board, the second board including a number of openings disposed in alignment with the contacts, wherein the adhesive layer and the second board position the contacts in a recessed location below the adhesive layer and the second layer within the electrical connector, and wherein the adhesive layer includes an aperture having a perimeter greater than an area surrounding the contacts on the first board and the openings in the second board.

13. The medical device of claim 12 wherein the medical device is a detector for a digital mammography imaging system.

* * * * *